United States Patent [19]

Meek, deceased et al.

[11] Plant 5,192

[45] Feb. 14, 1984

[54] CHRYSANTHEMUM PLANT

[75] Inventors: Jack M. Meek, deceased, late of Salinas, Calif.; by Saundra J. Meek, executrix, Canyon, Tex.; William E. Duffett, Salinas, Calif.

[73] Assignee: Yoder Brothers, Inc., Barberton, Ohio

[21] Appl. No.: 388,950

[22] Filed: Jun. 16, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar for cut spray culture known by the cultivar name Flair and characterized as to uniqueness by the combined characteristics of flat capitulum form; daisy capitulum type; dark red ray floret color, with maximum color oxidation; diameter across face of capitulum ranging from 75 to 85 mm. at maturity; uniform eight week photoperiodic flowering response to short days; medium peduncle length; medium plant height; tolerating 13° C. (55° F.) for initiation and development when grown as a single stem cut spray.

3 Drawing Figures

The present invention comprises a new and distinct cultivar of *Chrysanthemum morifolium,* Ramat., hereinafter referred to by the cultivar name Flair.

Flair is a product of a planned breeding program which had the objective of creating new chrysanthemum cultivars with daisy capitulum type, red ray floret color, eight or nine week flowering response, and having the ability to initiate and develop buds at 13° C. night temperature minimum and produce commercially acceptable quality in year round cut mum programs. Such traits in combination were not present in previously available commercial cultivars.

Flair was originated from a hybridization made in a controlled breeding program in Salinas, Calif. in 1977. The female parent was #75146024 (unnamed seedling) originated from a cross between Firepower (disclosed in U.S. Plant Pat. No. 3,947) and #73176013 (unnamed seedling). The male parent of Flair was #76003018 (unnamed seedling) which originated from a cross between #7407702 (unnamed seedling) and Accent (disclosed in U.S. Plant Pat. No. 3,945). Flair was discovered and selected as one flowering plant within the progeny of the stated parentage by William E. Duffett on Mar. 2, 1979 in a controlled environment in Salinas, Calif.

The first act of asexual reproduction of Flair was accomplished when vegetative cuttings were taken from the initial selection in June, 1979 in a controlled environment in Salinas, Calif. by a technician working under formulations established and supervised by Jack M. Meek. Horticultural examination of selected units initiated Nov. 26, 1979 has demonstrated that the combination of characteristics as herein disclosed for Flair are firmly fixed and are retained through successive generations of asexual reproduction.

Flair has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Flair which in combination distinguish this chrysanthemum as a new and distinct cultivar:

(1) flat caputulum form;

(2) daisy capitulum type;

(3) dark red ray floret color with minimum color oxidation;

(4) yellow-green (immature) to yellow (mature) disc floret color;

(5) diameter across face of capitulum ranging from 75 to 85 mm. at maturity;

(6) uniform eight week photoperiodic flowering response to short days;

(7) medium peduncle length, ranging from 80 to 100 mm.;

(8) medium plant height (requiring one to two long day weeks prior to short days to attain a flowered plant height of 80 to 90 cm. for May through October flowerings); and (9) low temperature tolerance of 13° C. (55° F.) for initiation and development when grown in single stem cut spray programs.

Of the many commercial cultivars known to the present inventors, the most similar in comparison to Flair is Dragon (disclosed in U.S. Plant Pat. No. 4,696). Reference is made to attached Chart A which compares certain characteristics of Flair to those same characteristics of Dragon. In comparison to Dragon, Flair has a smaller diameter across the face of the capitulum, shorter plant height, shorter peduncle length and a lower temperature tolerance for bud initiation and development. The capitulum form, capitulum type, ray floret color and flowering response are similar to those same characteristics of Dragon.

The accompanying photographic drawings show typical inflorescence and foliage characteristics of Flair, with colors being as nearly true as possible with illustrations of this type. Sheet 1 is a color photograph of Flair. Sheet 2 is a black and white photograph showing three views of the inflorescence of Flair. Sheet 3 is a black and white photograph showing the foliage of Flair at three stages of growth. The leaves illustrate both top and underside surfaces.

In the following description color references are made to The Royal Horticultural Society Colour Chart.

The color values were determined between 8:30 and 9:00 A.M. on Mar. 17, 1982 under 150 foot-candle light intensity at Salinas, Calif.

Classification:

*Botanical.*—*Chrysanthemum morifolium,* Ramat., CV Flair.

*Commercial.*—Cut daisy spray.

I. Inflorescence:

A. *Capitulum.*—Form: Flat. Type: Daisy. Diameter across face: 75 to 85 mm.

B. *Corolla of ray florets.*—Color (General Tonality from a Distance of Three Meters): dark red. Approximately 46A. Color (abaxial): (Immature) 46A to (Mature) 46B. Color (adaxial): 34C streaked with 46A.

C. *Corolla of disc florets.*—Color (mature): Approximately 13A. Color (immature): Approximately 144A.

D. *Reproductive organs.*—Androecium: Present disc florets only; scant pollen. Gynoecium: Present both ray and disc florets.

II. Plant:

A. *General appearance.*—Height: Medium, 50 to 60 cm. with no long days for May through October flowerings.

B. *Foliage.*—Color (abaxial): 137A. Color (adaxial): 146A. Shape: Very deeply lobed and coarsely serrated.

CHART A

| COMPARISON OF FLAIR AND DRAGON | | |
|---|---|---|
| | RAY FLORET | CAPITULUM |

CHART A-continued

| COMPARISON OF FLAIR AND DRAGON | | |
|---|---|---|
| CULTIVAR | COLOR | FORM AND TYPE |
| FLAIR | Dark Red | Flat Daisy |
| DRAGON | Dark Red | Flat Daisy |

| CULTIVAR | NO LONG DAYS PLANT HEIGHT | DIAMETER ACROSS FACE OF CAPITULUM | FLOWERING RESPONSE PERIOD |
|---|---|---|---|
| FLAIR | Medium 50 to 60 cm. | 75 to 85 mm. | 8 week |
| DRAGON | Tall 60 to 70 cm. | 90 to 100 mm. | 8 week |

| CULTIVAR | PEDUNCLE LENGTH | TEMPERATURE TOLERANCE |
|---|---|---|
| FLAIR | Medium 80 to 100 mm. | 13° C. |
| DRAGON | Long 125 to 155 mm. | 15° C. |

COMPARISONS MADE OF PLANTS GROWN AS SINGLE STEM CUT SPRAYS IN SALINAS, CALIFORNIA

We claim:

1. A new and distinct cultivar of *Chrysanthemum morifolium,* Ramat., plant known by the cultivar name Flair and particularly characterized as to uniqueness, as herein described and illustrated, by the combined characteristics of flat capitulum form; daisy capitulum type; dark red ray floret color, with minimum color oxidation; diameter across face of capitulum ranging from 75 to 85 mm. at maturity; uniform eight week photoperiodic flowering response to short days; medium peduncle length; medium plant height (when grown as a single stem cut spray); tolerating 13° C. (55° F.) for initiation and development when grown as a single stem cut spray.

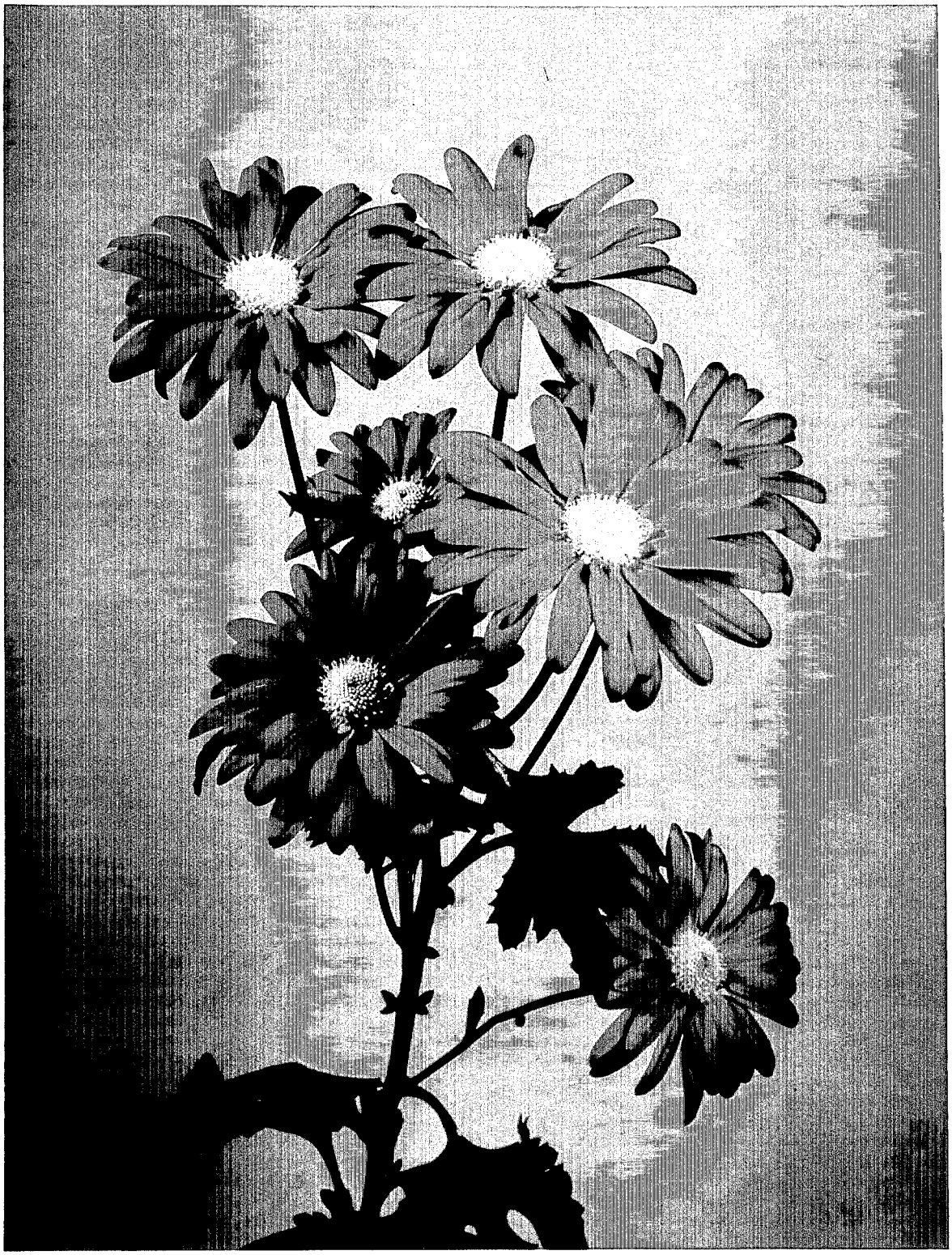

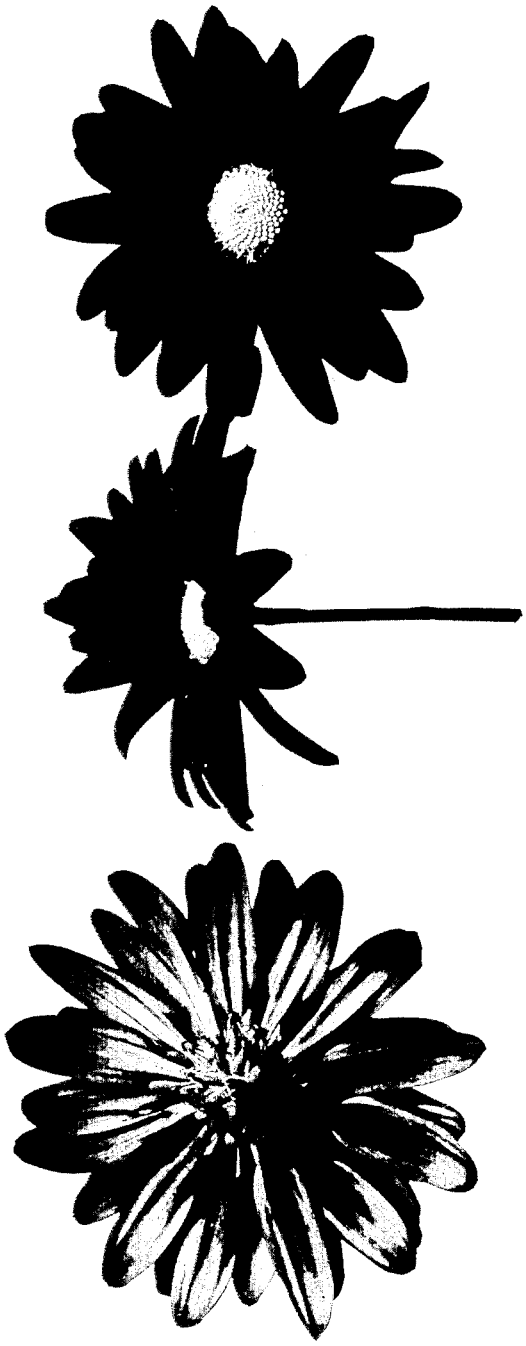

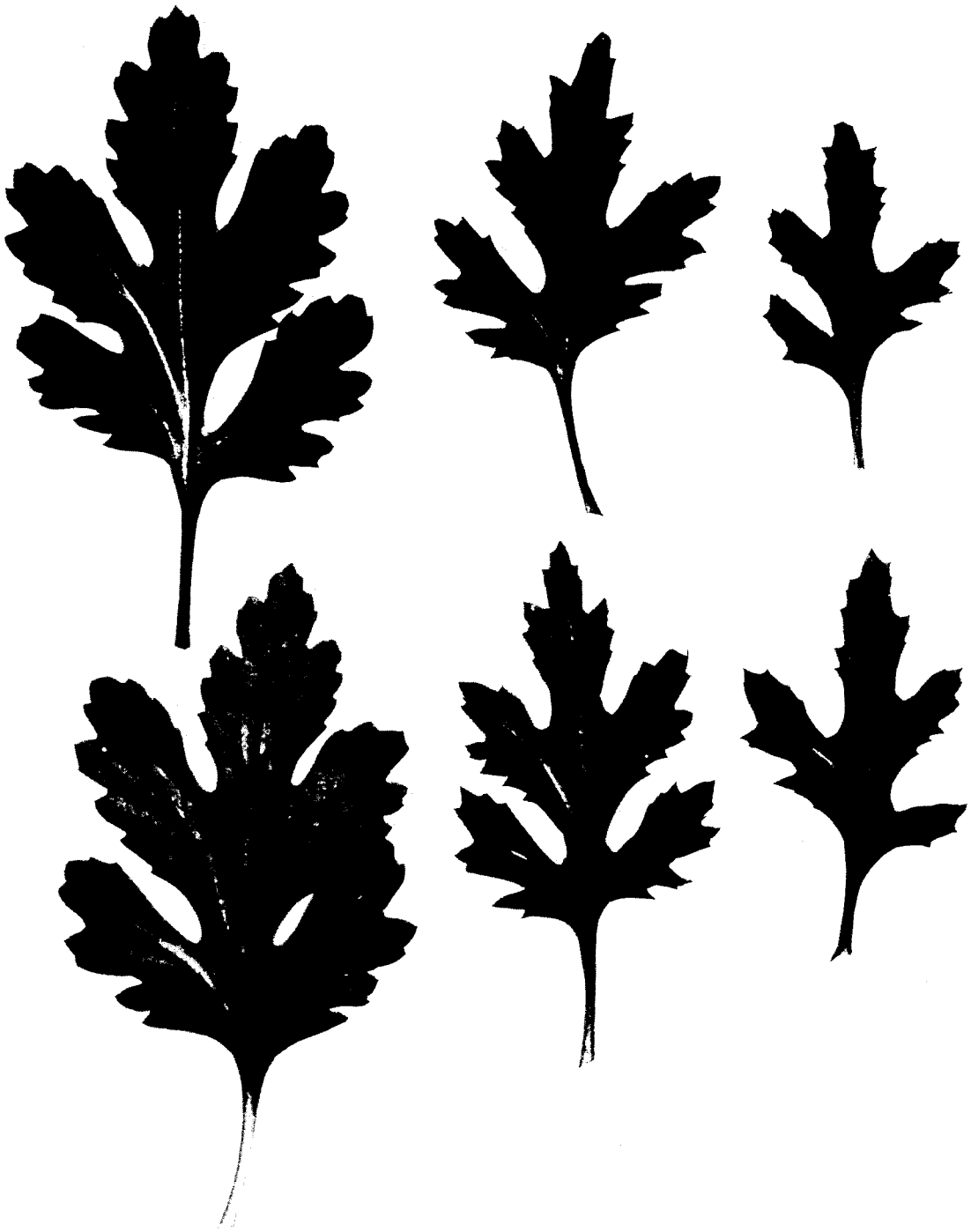

* * * * *